US00PP31942P3

(12) United States Plant Patent
Koekkoek

(10) Patent No.: US PP31,942 P3
(45) Date of Patent: Jul. 7, 2020

(54) CARNATION PLANT NAMED 'HILBECHAPELL'

(50) Latin Name: *Dianthus L.*
Varietal Denomination: Hilbechapell

(71) Applicant: Arthur N. J. Koekkoek, Alkmaar (NL)

(72) Inventor: Arthur N. J. Koekkoek, Alkmaar (NL)

(73) Assignee: Hilverda Kooij B.V., De Kwakel (NL)

( * ) Notice: Subject to any disclaimer, the term of this patent is extended or adjusted under 35 U.S.C. 154(b) by 0 days.

(21) Appl. No.: 16/501,651

(22) Filed: May 16, 2019

(65) Prior Publication Data

US 2019/0357400 P1 Nov. 21, 2019

Related U.S. Application Data

(60) Provisional application No. 62/762,743, filed on May 17, 2018.

(51) Int. Cl.
*A01H 5/02* (2018.01)
*A01H 6/30* (2018.01)

(52) U.S. Cl.
USPC ..... Plt./275
CPC ..... *A01H 6/305* (2018.05)

(58) Field of Classification Search
USPC ..... Plt./275
CPC ..... A01H 6/305; A01H 5/02
See application file for complete search history.

*Primary Examiner* — Keith O. Robinson
(74) *Attorney, Agent, or Firm* — C. A. Whealy

(57) ABSTRACT

A new and distinct cultivar of Carnation plant named 'Hilbechapell', characterized by its compact, upright to broadly spreading and uniformly mounding plant habit; freely branching habit; freely flowering habit; relatively large yellow green-colored double flowers; and good container and garden performance.

1 Drawing Sheet

Botanical designation: *Dianthus L.*
Cultivar denomination: 'HILBECHAPELL'.

BACKGROUND OF THE INVENTION

The present invention relates to a new and distinct cultivar of Carnation plant, botanically known as *Dianthus L.*, grown commercially as a container plant and hereinafter referred to by the name 'Hilbechapell'.

The new Carnation plant is a product of a planned breeding program conducted by the Inventor in De Kwakel, The Netherlands. The objective of the breeding program is to create new container Carnation plants with numerous attractive flowers.

The new Carnation plant originated from a cross-pollination made by the Inventor in De Kwakel, The Netherlands in May, 2012 of *Dianthus L.* 'Mel', not patented, as the female, or seed, parent with a proprietary selection of *Dianthus L.* identified as code number 1306, not patented, as the male, or pollen, parent. The new Carnation plant was discovered and selected by the Inventor as a single flowering plant from within the progeny of the stated cross-pollination in a controlled greenhouse environment in De Kwakel, The Netherlands in June, 2013.

Asexual reproduction of the new Carnation plant by terminal cuttings propagated in a controlled greenhouse environment in De Kwakel, The Netherlands since March, 2014 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilbechapell'. These characteristics in combination distinguish 'Hilbechapell' as a new and distinct Carnation plant:

1. Compact, upright to broadly spreading and uniformly mounding plant habit.
2. Freely branching habit.
3. Freely flowering habit.
4. Relatively large yellow green-colored double flowers.
5. Good container and garden performance.

Plants of the new Carnation differ primarily from plants of the female parent, 'Mel', in the following characteristics:

1. Plants of the new Carnation grow faster than plants of 'Mel'.
2. Flowers of plants of the new Carnation have more petaloids than flowers of plants of 'Mel'.
3. Flower petals of plants of the new Carnation are not as deeply incised as flower petals of plants of 'Mel'.
4. Flowers of plants of the new Carnation are yellow green in color whereas flowers of plants of 'Mel' are yellow and pink in color.

Plants of the new Carnation differ primarily from plants of the male parent selection in the following characteristics:

1. Plants of the new Carnation are more compact and grow slower than plants of the male parent selection.
2. Plants of the new Carnation have larger flowers than plants of the male parent selection.
3. Flowers of plants of the new Carnation are yellow green in color whereas flowers of plants of the male parent selection are dark red in color.

Plants of the new Carnation also can be compared to plants of *Dianthus caryophyllus* 'Mel Orange', not patented. In side-by-side comparisons, plants of the new Carnation differ primarily from plants of 'Mel Orange' in the following characteristics:

1. Plants of the new Carnation grow faster than plants of 'Mel Orange'.
2. Flowers of plants of the new Carnation have more petaloids than flowers of plants of 'Mel Orange'.
3. Flower petals of plants of the new Carnation are not as deeply incised as flower petals of plants of 'Mel Orange'.
4. Flowers of plants of the new Carnation are yellow green in color whereas flowers of plants of 'Mel Orange' are orange in color.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant. The photograph comprises a side perspective view of a typical flowering plant of 'Hilbechapell' grown in a container.

DETAILED BOTANICAL DESCRIPTION

Plants used in the aforementioned photograph and following observations and measurements were grown during the spring in 11.5-cm containers in a glass-covered greenhouse in De Kwakel, The Netherlands and under cultural practices typical of commercial container Carnation production. During the production of the plants, day temperatures ranged from 16° C. to 20° C. and night temperatures ranged from 16° C. to 18° C. Plants used for the photograph and description were 13 weeks from planting and were pinched one time at the time of planting. In the following description, color references are made to The Royal Horticultural Society Colour Chart, 2015 Edition, except where general terms of ordinary dictionary significance are used.

Botanical classification: *Dianthus caryophyllus* 'Hillbechapell'.

Parentage:

*Female, or seed, parent.*—*Dianthus L.* 'Mel', not patented.

*Male, or pollen, parent.*—Proprietary selection of *Dianthus L.* identified as code number 1306, not patented.

Propagation:

*Type.*—By terminal vegetative cuttings.

*Time to initiate roots, summer.*—About six days at temperatures ranging from 20° C. to 25° C.

*Time to initiate roots, winter.*—About eight days at temperatures about 18° C.

*Time to produce a rooted young plant, summer.*—About three weeks at temperatures ranging from 20° C. to 25° C.

*Time to produce a rooted young plant, winter.*—About five weeks at temperatures about 18° C.

*Root description.*—Medium in thickness, fibrous; white in color, actual color of the roots is dependent on substrate composition, water quality, fertilizer type and formulation, substrate temperature and physiological age of roots.

*Rooting habit.*—Moderate branching; medium density.

Plant description:

*Plant and growth habit.*—Herbaceous perennial, typically grown as a container plant; compact, uniformly mounding, upright to broadly spreading plant habit; moderately vigorous growth habit; slow to moderate growth rate.

*Plant height, soil level to top of foliar plane.*—About 11.5 cm.

*Plant height, soil level to top of floral plane.*—About 13.1 cm.

*Plant diameter or spread.*—About 21.3 cm.

*Lateral branches.*—Branching habit: Freely branching habit with about six main (basal) stems; each main stem with about four lateral branches; pinching is not required, however, pinching will enhance lateral branch development. Length: About 9.7 cm. Diameter: About 3.5 mm. Internode length: About 1.5 cm. Strength: Strong. Aspect: Upright to about 60° from vertical. Texture and luster: Smooth, glabrous, waxy cuticle; matte. Color, developing: Close to 142C; at internodes, close to 145B. Color, developed: Close to 147A; thin waxy cuticle, close to 188A.

Leaf description:

*Arrangement.*—Opposite, simple; sessile.

*Length.*—About 9 cm.

*Width.*—About 9 mm.

*Shape.*—Narrowly lanceolate; slightly carinate; strongly curled.

*Apex.*—Acute.

*Base.*—Attenuate; decurrent.

*Margin.*—Entire; not lobed.

*Texture and luster, upper and lower surfaces.*—Smooth, glabrous; waxy cuticle; matte.

*Venation pattern.*—Parallel.

*Color.*—Developing leaves, upper and lower surfaces: Close to 138A. Fully expanded leaves, upper surface: Close to N189A; waxy cuticle, close to N189B; venation, close to N189A. Fully expanded leaves, lower surface: Close to NN137A; waxy cuticle, close to 189A; venation, close to 143A.

Flower description:

*Flower form and flowering habit.*—Rotate double-type flowers arranged singly or in pairs; freely flowering habit with about 56 open flowers per plant at one time; flowers face mostly upright to slightly outwardly.

*Natural flowering season.*—Flowering is continuous from the spring to late summer in The Netherlands; plants begin flowering about 13 weeks after planting.

*Postproduction longevity.*—Flowers last about ten days on the plant; flowers not persistent.

*Fragrance.*—Moderately fragrant; clove-like, sweet and pleasant.

*Flower buds.*—Length: About 2.1 cm. Diameter: About 1.4 cm. Shape: Broadly elliptic to broadly obovate. Texture and luster: Smooth, glabrous; matte. Color: Close to 143A; towards the base, close to 143C.

*Flower diameter.*—Relatively large, about 5.8 cm.

*Flower depth.*—About 4.4 cm.

*Petals.*—Quantity and arrangement: About five petals arranged in a single whorl. Length: About 3.8 cm.

Width: About 2.3 cm. Shape: Spatulate. Apex: Irregularly dentate and praemorse. Base: Narrowly cuneate. Margin: Distally, irregularly and finely dentate; proximally, entire; moderately undulate. Texture and luster, upper and lower surfaces: Smooth, glabrous; velvety; matte. Color: When opening, upper and lower surfaces: Close to 1C; towards the margins, close to 2D; towards the base, close to 145C. Fully opened, upper surface: Close to 150C; towards the margins, close to 1D; at the base, close to 145C; main vein, close to 145A to 145B; secondary venation, similar to lamina colors; color does not change with development. Fully opened, lower surface: Close to 145C; towards the margins, close to 150C to 150D; at the base, close to 145B; venation, similar to lamina colors; colors do not change with development.

*Petaloids.*—Quantity and arrangement: About 80 petaloids arranged in about eight whorls. Length: About 2.3 cm to 3.7 cm. Width: About 0.5 cm to 2 cm. Shape: Spatulate. Apex: Irregularly dentate and praemorse. Base: Narrowly cuneate. Margin: Distally, irregularly and finely dentate; proximally, entire; moderately to highly undulate. Texture and luster, upper and lower surfaces: Smooth, glabrous; velvety; matte. Color: When opening, upper and lower surfaces: Close to 1C; towards the margins, close to 2D; towards the base, close to 145C. Fully opened, upper surface: Close to 150C; towards the margins, close to 1D; at the base, close to 145C; main vein, close to 145A to 145B; secondary venation, similar to lamina colors; color does not change with development. Fully opened, lower surface: Close to 145C; towards the margins, close to 150C to 150D; at the base, close to 145B; venation, similar to lamina colors; colors do not change with development.

*Sepals.*—Quantity and arrangement: Five sepals arranged in a single whorl; proximal 70% portion of the sepals are fused into a campanulate-shaped calyx. Calyx length: About 2.5 cm. Calyx diameter: About 2.2 cm. Sepal length: About 2.5 cm. Sepal width, at base of "free" portion: About 9 mm. Shape: Obovate. Apex: Broadly acute. Margin: Entire. Texture and luster, upper and lower surfaces: Smooth, glabrous; slightly glossy. Color: When opening, upper surface: Close to 147D. When opening, lower surface: Close to 137A and 137B; towards the base, close to 144B. Fully opened, upper surface: Close to 192B to 192C; at the apex and base, close to 147D. Fully opened, lower surface: Close to 137A; towards the base, close to 144B.

*Peduncles.*—Length: About 5 mm. Diameter: About 4 mm. Strength: Moderately strong. Aspect: About 30° from the stem axis. Texture and luster: Smooth, glabrous, waxy; matte. Color: Close to 147A; thin waxy layer, close to 188A.

*Reproductive organs.*—Stamens: Quantity: About 50; significantly deformed. Filament length: About 0.5 cm to 1.2 cm. Filament color: Close to 157C to 157D. Anther size: About 0.5 mm by 1.5 mm. Anther shape: Irregularly oblong, deformed. Anther color: Close to 161D. Pollen: None observed to date. Pistils: Quantity: About three per flower. Pistil length: About 2.4 cm. Stigma diameter: About 1 mm. Stigma shape: Pointed, curved. Stigma color: Close to 155A. Style length: About 2.3 cm. Style color: Close to between 155C and 157D. Ovary color: Close to 144D. Fruits and seeds: To date, fruit and seed development have not been observed on plants of the new Carnation.

Pathogen & pest resistance: To date, plants of the new Carnation have not been observed to be resistant to pathogens and pests common to Carnation plants.

Garden performance: Plants of the new Carnation have been observed to tolerate rain, wind, high temperatures about 35° C. and to be suitable for USDA Hardiness Zones 5 to 9.

It is claimed:

1. A new and distinct Carnation plant named 'Hilbechapell' as illustrated and described.

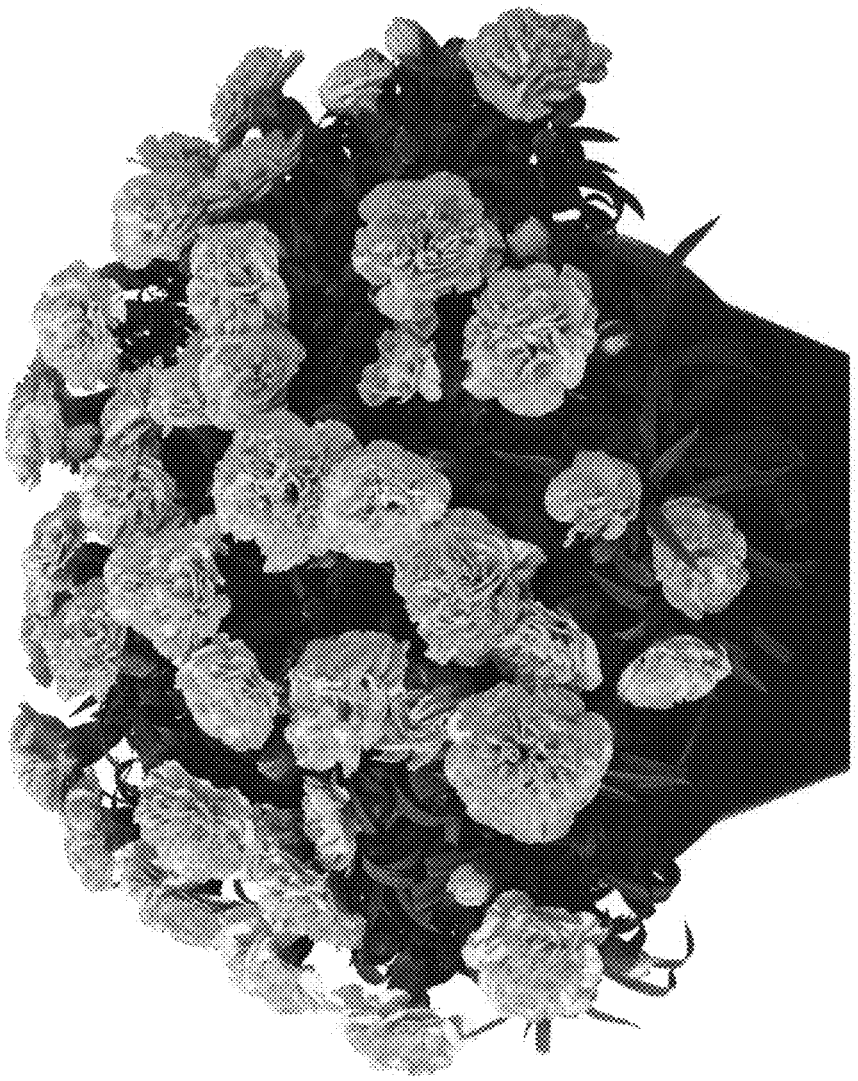

* * * * *